United States Patent
Chao et al.

(10) Patent No.: US 7,111,985 B2
(45) Date of Patent: Sep. 26, 2006

(54) METHOD AND SYSTEM FOR MEASURING TABLE SAG

(75) Inventors: Edward Henry Chao, Oconomowoc, WI (US); Wolfgang Just, Riverwood (AU); Ariel Friedlander, Mequon, WI (US)

(73) Assignee: General Electric Company, Schenectady, NY (US)

( * ) Notice: Subject to any disclaimer, the term of this patent is extended or adjusted under 35 U.S.C. 154(b) by 77 days.

(21) Appl. No.: 10/982,325

(22) Filed: Nov. 4, 2004

(65) Prior Publication Data

US 2006/0093093 A1    May 4, 2006

(51) Int. Cl.
*G01D 18/00* (2006.01)
(52) U.S. Cl. ..................... 378/207; 382/131
(58) Field of Classification Search ............. 378/207; 382/131, 132
See application file for complete search history.

(56) References Cited

U.S. PATENT DOCUMENTS

| | | | |
|---|---|---|---|
| 5,777,332 A | 7/1998 | Lonn et al. | 250/363.4 |
| 6,143,003 A | 11/2000 | Cosman | 606/130 |
| 6,561,695 B1 | 5/2003 | Proska | 378/207 |
| 6,565,577 B1 | 5/2003 | Cosman | 606/130 |
| 6,700,949 B1 | 3/2004 | Susami et al. | 378/19 |
| 2002/0081008 A1 | 6/2002 | Wollenweber | 382/131 |
| 2002/0122575 A1 | 9/2002 | Vaisburd et al. | 382/131 |

*Primary Examiner*—Courtney Thomas
(74) *Attorney, Agent, or Firm*—Cantor Colburn LLP

(57) ABSTRACT

A method for measuring table sag of a table may include utilizing images of an unloaded table and a loaded table, plotting pixel values for a range of pixels for each image within a particular column, identifying a pixel within each plot that has a highest pixel value, calculating a difference between the identified pixel row numbers, and converting the difference into a measurement of table sag. A storage medium encoded with machine-readable computer program code for measuring table sag of a table may include instructions for causing a computer to implement the method. A computer for use in an imaging system may utilize digital images for the measurement of table sag and an imaging system may include such a computer.

23 Claims, 7 Drawing Sheets

METHOD AND SYSTEM FOR MEASURING TABLE SAG

BACKGROUND OF THE INVENTION

This invention relates generally to a method and system for measuring table sag, and more particularly, this invention relates to an improved method and system for measuring sag of a loaded table used in imaging systems.

In a computed tomography (CT) system, an x-ray source projects a fan-shaped beam that is collimated to lie within an X-Y plane of a Cartesian coordinate system, termed the "imaging plane." The x-ray beam passes through the object being imaged, such as a medical patient, and impinges upon a multi-row multi-column detector array. The detector array comprises a plurality of detector elements. The intensity of the transmitted radiation is dependent upon the attenuation of the x-ray beam by the object and each detector element of the detector array produces a separate electrical signal that is a measurement of the beam attenuation. The attenuation measurements from all of the detector elements are acquired separately to produce the transmission profile.

The source and detector array in a conventional CT system are rotated on a gantry within the imaging plane around the object so that the angle at which the x-ray beam intersects the object constantly changes. A group of x-ray attenuation measurements from the detector array at a given angle is referred to as a "view" and a "scan" of the object comprises a set of views made at different angular orientations during one revolution of both the x-ray source and the detector. In an axial scan, the projection data is processed to construct an image that corresponds to a two-dimensional slice taken through the object. One method for reconstructing an image from a set of projection data is referred to as the filtered back projection technique. This process converts the attenuation measurements from a scan into integers called "CT numbers" or "Hounsfield units", which are used to control the brightness of the corresponding pixel on a cathode ray tube display.

A detector array in a CT imaging system comprises a plurality of detector modules. Each detector module has a scintillator array optically coupled to a semiconductor photodiode array. The scintillator array emits light in response to receiving x-rays. The photodiode array detects light output by the scintillator array and generates electrical signals responsive thereto.

When acquiring CT images, it is important to have precise patient and image registration. For radiation treatment (RT) planning purposes, it is desired to scan the patient on the CT scanner in the exact position that will be used for radiation treatment. Third party laser lights are often installed and calibrated in order to assist with this patient positioning. The $3^{rd}$ party laser lights are usually installed a substantial distance (~0.6 m) from the scanning plane and a noticeable amount of vertical table sag can occur between the table position used to align the patient with the third party lights and the table position used while acquiring the CT scan. This table sag, if unaccounted for, could result in errors in the radiation treatment. Table sag distances as large as 6 mm have been measured at clinical sites.

U.S. Pat. No. 6,561,695 addresses several patient and image registration inaccuracies, including table sag. However, the method requires special equipment to be installed in tables. Thus, previous methods have used additional hardware that gives geometrical information including table sag and special tables must be purchased and installed for conducting such methods.

BRIEF DESCRIPTION OF THE INVENTION

Disclosed herein, in an exemplary embodiment, is a method for measuring table sag of a table, the method including identifying pixel values of pixels from a column in a loaded table image and in an unloaded table image and calculating a difference between pixel row numbers having highest pixel values in the loaded table image and unloaded table image for determining how many pixel rows the table has sagged from the unloaded image to the loaded image.

Also disclosed herein, in another exemplary embodiment, is a storage medium encoded with machine-readable computer program code for measuring table sag of a table, the storage medium including instructions for causing a computer to implement the above-described method.

Also disclosed herein, in another exemplary embodiment, is a computer for use in an imaging system, the computer for receiving digital images from an image reconstructor in the imaging system, wherein table sag, of a table used within the imaging system, is calculated only within the computer using information provided from the digital images received by the computer.

Further disclosed herein, in another exemplary embodiment, is an imaging system including an x-ray source, an x-ray detector array for receiving an x-ray beam from the x-ray source, a data acquisition system for receiving signals from the x-ray detector array, an image reconstructor for receiving signals from the data acquisition system and for generating digital images, a table for supporting a person or object adjacent the x-ray source, and a computer for receiving the digital images from the image reconstructor, wherein table sag is calculated only within the computer using information provided from the digital images.

DETAILED DESCRIPTION OF THE INVENTION

Figure 1:
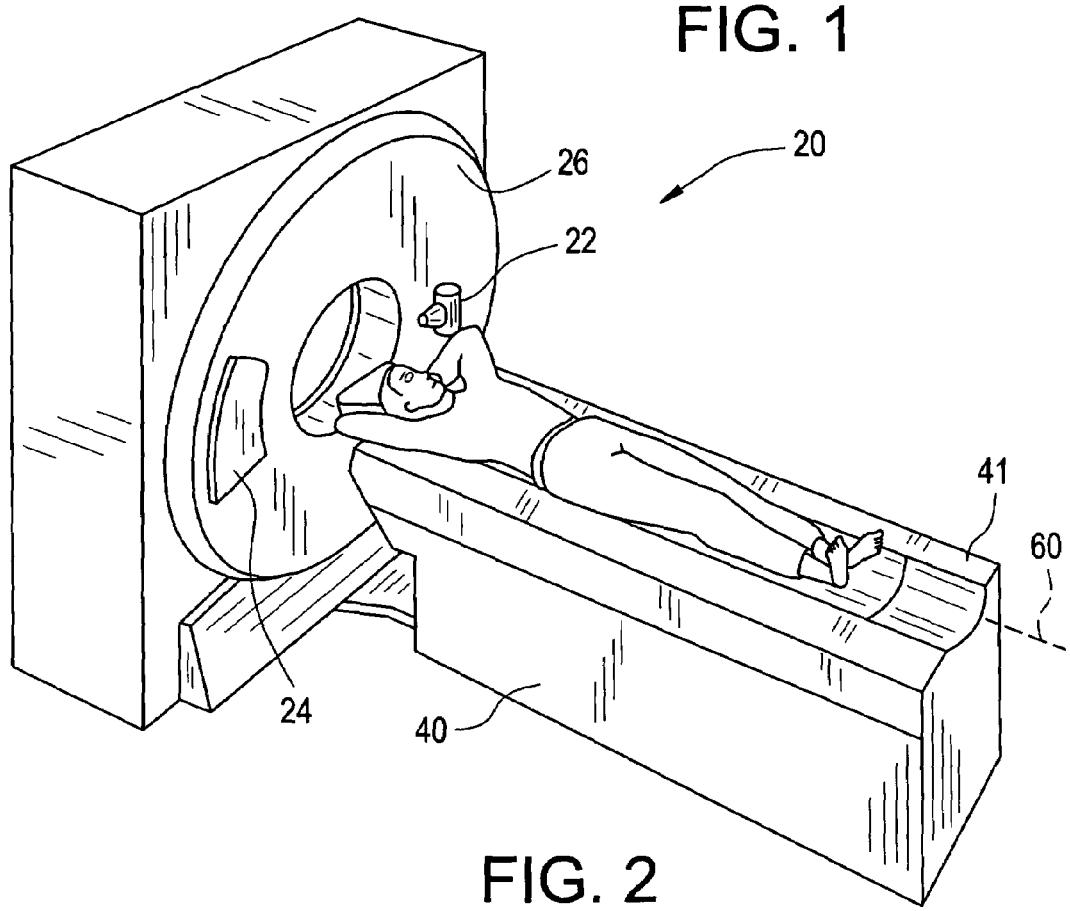
FIG. 1 is a schematic of a CT imaging system in accordance with exemplary embodiment.
Figure 2:
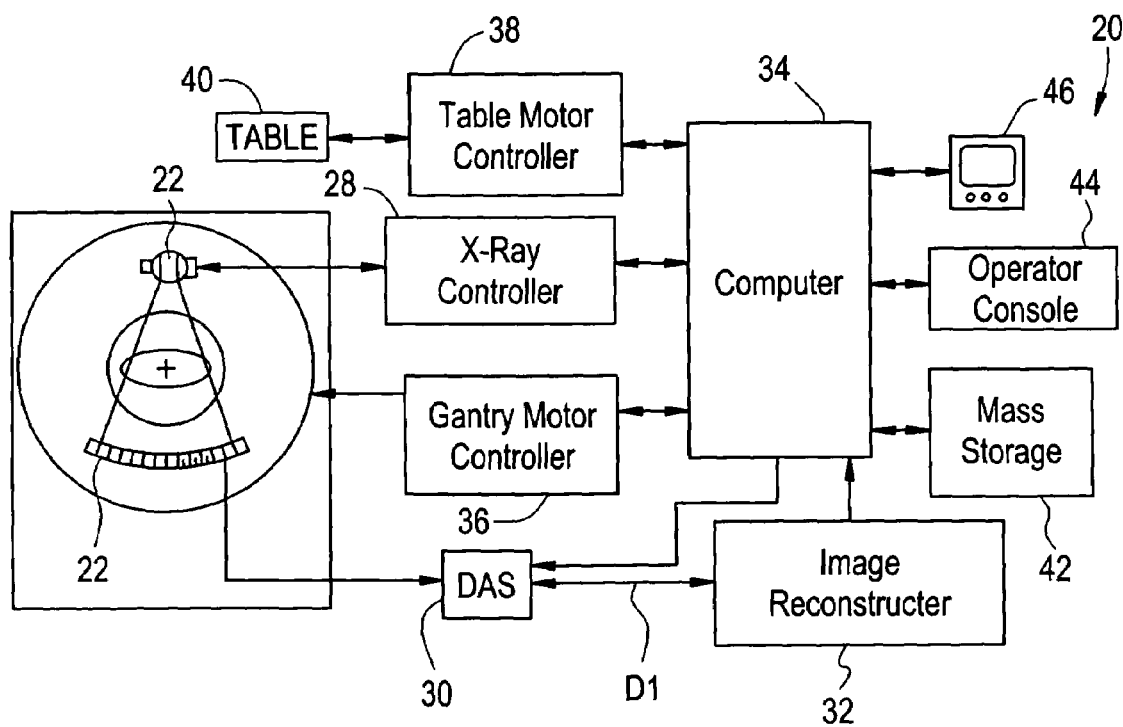
FIG. 2 is a more detailed schematic of the CT imaging system of FIG. 1.

Referring to FIGS. 1 and 2, a CT imaging system 20 for generating digital images of a person in accordance with an exemplary embodiment is shown. The CT imaging system 20 includes up an x-ray source 22, an x-ray detector array 24, a gantry 26, an x-ray controller 28, a data acquisition system 30, an image reconstructor 32, a computer 34, a gantry motor controller 36, a table motor controller 38, a table 40, a mass storage unit 42, an operator console 44, and a monitor 46.

The x-ray source 22 is provided to generate a fan-shaped x-ray beam that propagates through a person to the x-ray detector array 24. The x-ray source 22 is disposed on the gantry 26.

Referring to FIG. 2, the gantry 26 is provided to support the x-ray source 22 and the x-ray detector array 24. In particular, the x-ray source 22 is disposed across from the x-ray detector 24 on the gantry 26. The gantry motor controller 36 induces the gantry 26 to rotate both the x-ray source 22 and the x-ray detector array 24 at a predetermined rotational speed in response to a control signal received from the computer 34.

The x-ray controller 28 is provided to control the operation of the x-ray source 22. The x-ray controller 28 is operably coupled to the x-ray source 22 and to the computer 34. The x-ray controller 28 energizes the x-ray source 22 to emit x-ray beams in response to a control signal received from the computer 34.

The data acquisition system 30 is operably coupled to the x-ray detector array 24 and is further operably coupled to the computer 34 and to the image reconstructor 32. The data acquisition system 30 receives signals (D1) from the x-ray detector array 24 and transmits the signals to the image reconstructor 32.

The image reconstructor 32 is provided to generate digital images from the signals (D1). The image reconstructor 32 is operably coupled between the data acquisition system 30 and the computer 34. The image reconstructor 32 transmits the generated digital images to the computer 34.

The gantry motor controller 36 is provided to control the rotational position of the gantry 26. As shown, the gantry motor controller 36 is operably coupled to the gantry 26 and to the computer 34. The gantry motor controller 36 generates control signals that induce a motor (not shown) within the gantry 26 to rotate the gantry 26 at a predetermined rotational speed, in response to a control signal received from the computer 34.

The table motor controller 38 is provided to control a linear position of a plate 41 disposed on the table 40. In particular, the table motor controller 38 generates control signals that induce a linear actuator (not shown) within the table 40 to move the plate 41 to a predetermined linear position, in response to a control signal received from the computer 34. A top of the plate 41 corresponds to a "table surface" as will be further described below with respect to the method and system for measuring table sag.

The computer 34 is operably coupled to the x-ray controller 28, the data acquisition system 30, the image reconstructor 32, the gantry motor controller 36, the table motor controller 38, the external memory 42, the operator console 44, and the computer console 46. The computer 34 generates a first control signal for inducing the table motor controller 38 to control position of the table 40. The control computer 132 generates a second control signal for inducing the x-ray controller 28 to induce x-ray source 22 to generate x-ray beams. Further, the computer 34 generates a third control signal for inducing the gantry motor controller 36 to rotate the gantry 26. Further, the computer 34 generates a fourth control signal to induce the data acquisition system 30 to sample signals received from the x-ray detector array 24. In response, the system 30 transmits the signals received from the x-ray detector array 24 to the image reconstructor 32. Thereafter, the image reconstructor 32 generates digital images based upon the signals received from the data acquisition system 30 and transmits the digital images to the computer 34. The computer 34 displays the images on the monitor 46 or stores the digital images in the mass storage unit 42, or both. The operator console 44 is operably coupled to the computer 32 to allow user to request specific digital images for viewing.

Figure 3:
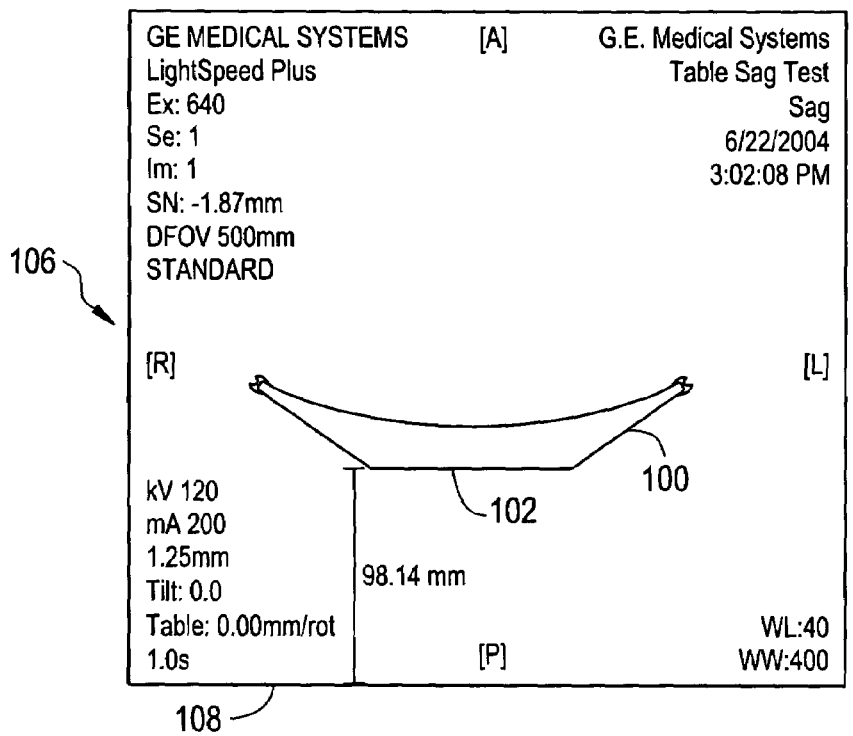
FIG. 3 is an image of an unloaded table.
Figure 4:
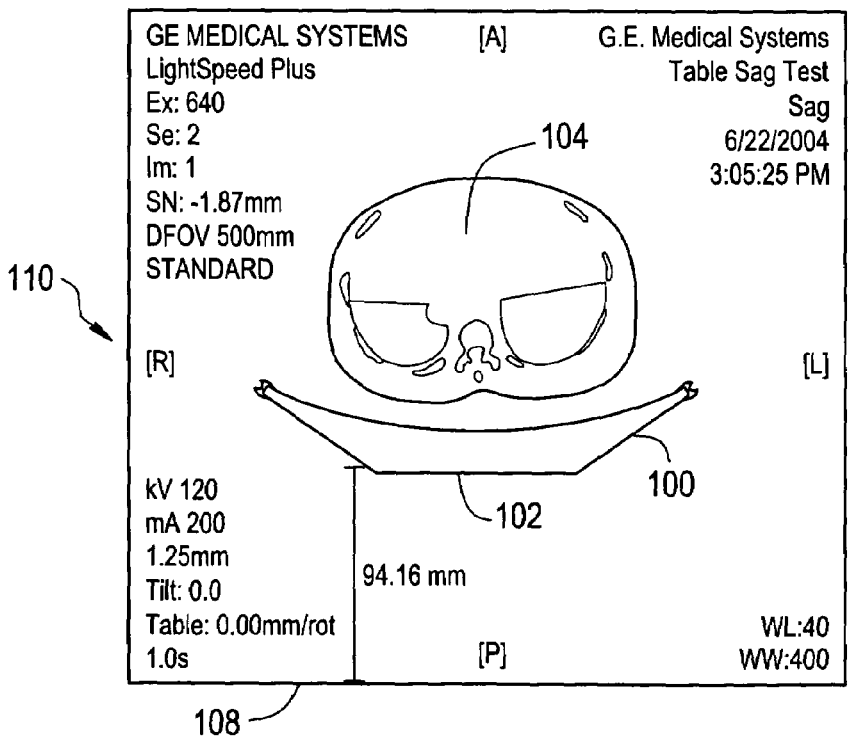
FIG. 4 is an image of a loaded table.

The problem of table sag may be reproduced in an engineering bay by scanning a table 100, without any weight on it as shown in FIG. 3, and then scanning it again with an anatomical phantom 104 placed on the table 100, as shown in FIG. 4. In FIG. 3, the distance from the bottom 108 of the image 106 to the bottom 102 of the unloaded table 100 is 98.14 mm. When an anatomical chest phantom 104 is placed on the table 100, as shown in FIG. 4, (along with an anatomical pelvis phantom), the distance from the bottom 108 of the image 110 is now only 94.16 mm, signifying a sag in the table 100 of almost 4 mm. In this particular example, the anatomical phantom 104 is equivalent to a relatively small person. A large person could cause the table 100 to sag significantly further.

Figure 11:
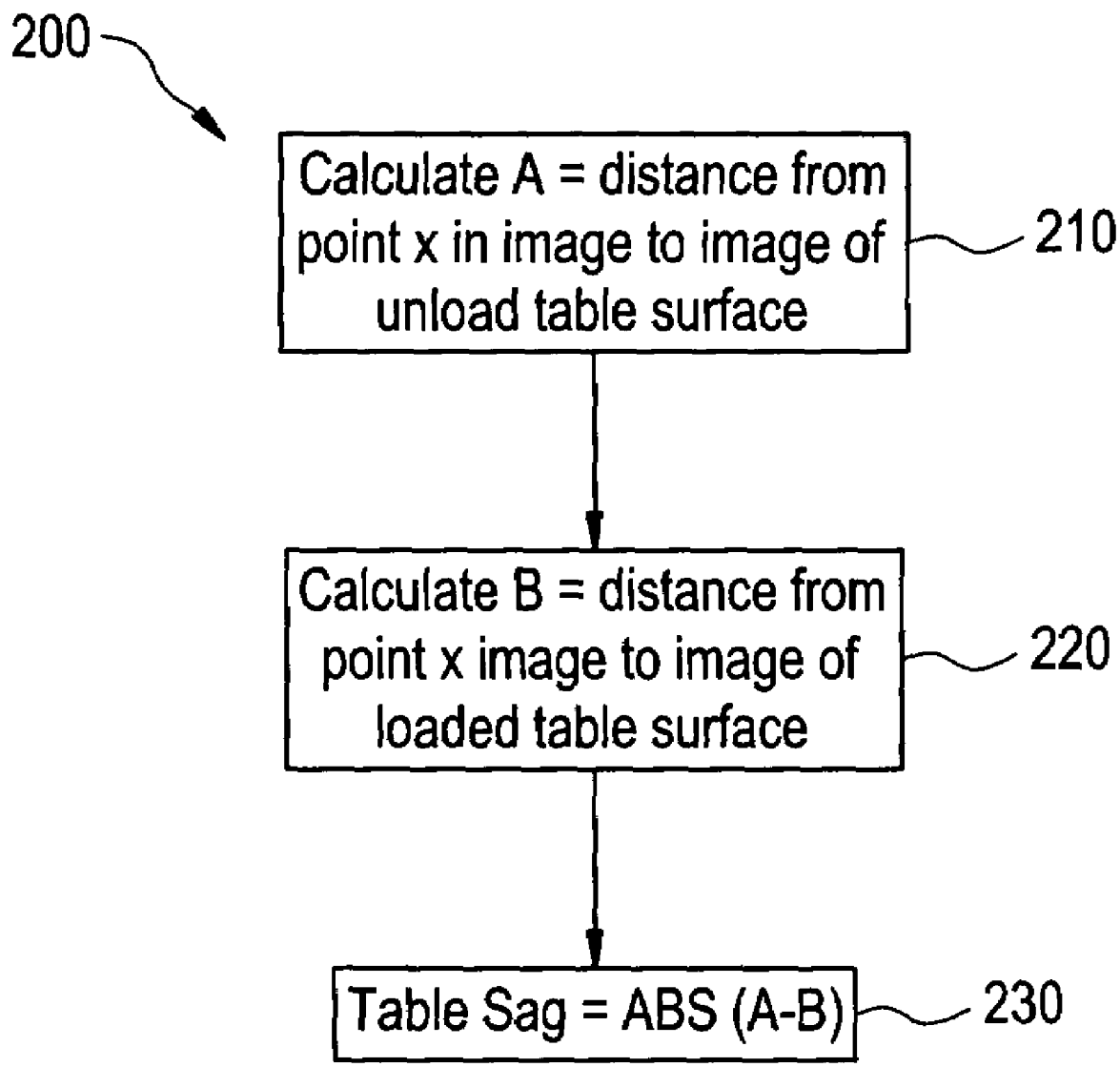
FIG. 11 is a flowchart of a method of measuring table sag.

The method 200 of estimating table sag as described with respect to FIGS. 3 and 4 is demonstrated in FIG. 11. The method 200 includes step 210 where the distance A is calculated from a point x in the image to an image of unloaded table surface. In the description of FIGS. 3–4, the point x was the bottom 108 of the image 110, although other points within the image are within the scope of this method. The step 220 calculates the distance B from the same point x within the image 110 to the image of the loaded table surface. The step 230 calculates table sag by taking the absolute value of A minus B. If the bottom 108 of the image 110 is used as the point x, then the difference between A and B would be table sag, but if the point x is chosen above the table surface, then the table sag would be B minus A.

It should be noted that the method 200 of estimating table sag demonstrated in FIG. 11 and FIGS. 3 and 4 is a clear demonstration that the problem of table sag exists, however automatically performing such a graphical measurement may be difficult to execute since the distance from the top of the image to the bottom of the image may vary depending on scanners, and in most scanners an operator is able to "target" or zoom-in the reconstruction so that the distance from the top to the bottom is much smaller. Thus, such a method would have to compensate for the fact that the bottom of the image may change location during use.

Figure 5:
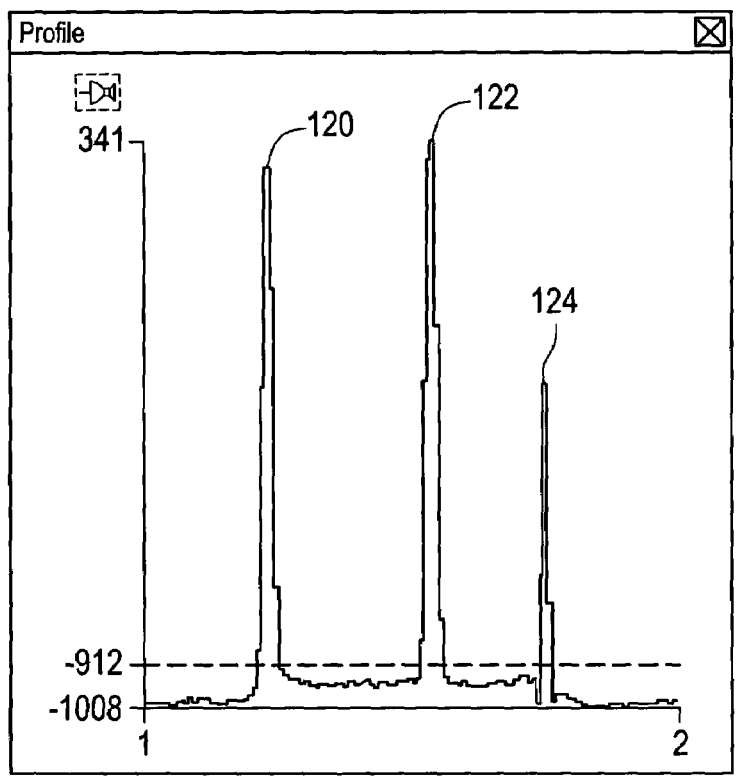
FIG. 5 is a profile of pixel values showing peaks corresponding to table surfaces.
Figure 6:
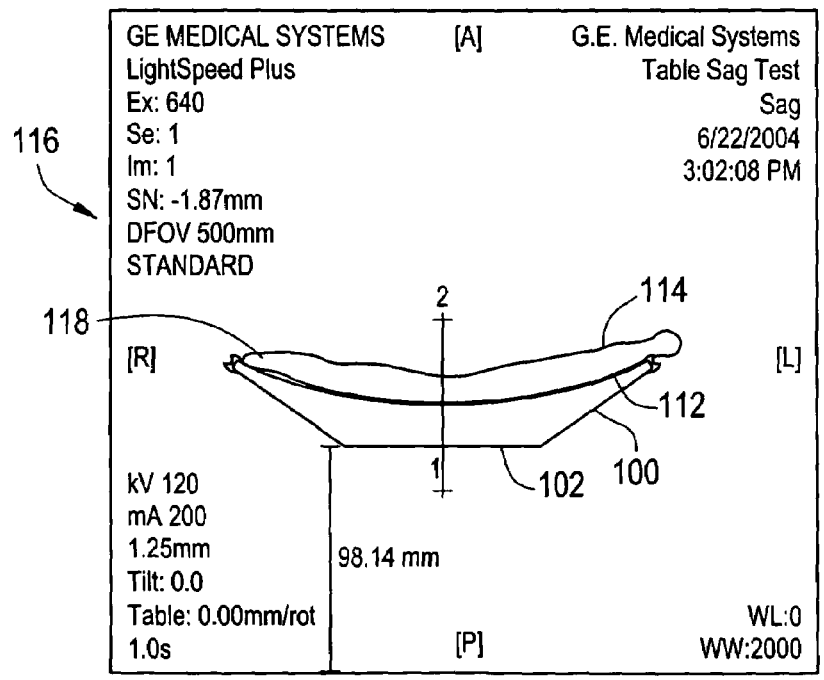
FIG. 6 is an image of an unloaded table used for producing the profile of FIG. 5.

Most CT patient tables in use today are uniform in the axial (z) direction in order to avoid creating artifacts. Additionally, they are often manufactured of a low density volume substance to avoid attenuating the X-ray signal, together with a higher density surface material. These properties allow use of the CT table surface as a reference for measuring the vertical table position. In particular, on the scanner of these embodiments, the table surfaces show up in the CT images (e.g., images 106 in FIG. 3 and 110 in FIG. 4) as thin lines. These thin lines are simple to detect and may be used as a calibration marker in the vertical direction. In FIG. 5, a plot is shown of the pixel values along line 1-2 from FIG. 6 that passes through the table surfaces 102, 112, and 114 shown in FIG. 6. Reading the plot in FIG. 5 in the x direction from "1" to "2", the first two peaks 120, 122 correspond to the bottom and top table surfaces 102, 112, respectively, while the third peak 124 marks the surface 114 of the table padding 118. The peaks 120, 122, and 124 are well defined making detection straightforward. Either the center or the edges of the peaks 120, 122, 124 may be used as reference points. With either method, the error in calculating the surface locations will likely be substantially less than +/−1 pixel. For the 50 cm field of view used in FIG. 6 (DFOV=500 mm), +/−1 pixel of error corresponds to +/−0.98 mm.

In order to correct for variable amounts of table sag, an algorithm is described that searches through a vertical set of image pixels to find the table surface locations. By a "vertical set", it should be understood that such a set would include pixels lying along a line connecting the top and bottom of the image, such as a line extending from [A] to [P] in FIG. 6 (where [A] and [P] represent anterior and posterior), and such as line 1-2. This vertical set of pixels may be referenced with respect to a constant scanner location such as the scanner isocenter, so that targeted reconstructions do not affect the algorithm. By "targeted reconstructions" it should be understood that an operator may view an image of a pre-selected field, smaller than the entirely available image. In order to reduce the possibility of errors, the set of pixels may be further restricted by using table height information stored in the DICOM image header (field 0018–1130 of the Digital Imaging and Communications in Medicine standard), not shown in the figures. This information can be used to predict the pixel location of the table surfaces with no sag.

For example, the table height field for the images may contain the number 100.2, indicating the predicted table surface is 100.2 mm below isocenter. The number is not shown in the images, as it may be stored in a data file along with the image data. The number 100.2 may indicate the top of a bare table surface. For a 50 cm display field of view ("DFOV"), this translates to 102.6 pixels below isocenter (100.2 mm/(500 mm/512 pixels)=102.6 pixels). Since this image was not targeted, the isocenter is located at pixels (256.5, 256.5), mid-way between the center 4 pixels. The images described herein are composed of 512×512 pixels, however other image constructions are within the scope of these methods. In this particular method, these 512×512 pixels cover a 500 mm×500 mm area (50 cm DFOV). Thus, there are 500 mm/512 pixels or 0.976 mm/pixel. Of course, if the DFOV changes, then the mm/pixel likewise changes. For a targeted reconstruction, the isocenter location may be calculated from the information in the DICOM header. For the example image, the top table surface is thus predicted to be at pixel row 359, because 256.5+102.6=359.1. It should also be noted that the same method may be employed for any of the other table surfaces.

Figure 7:
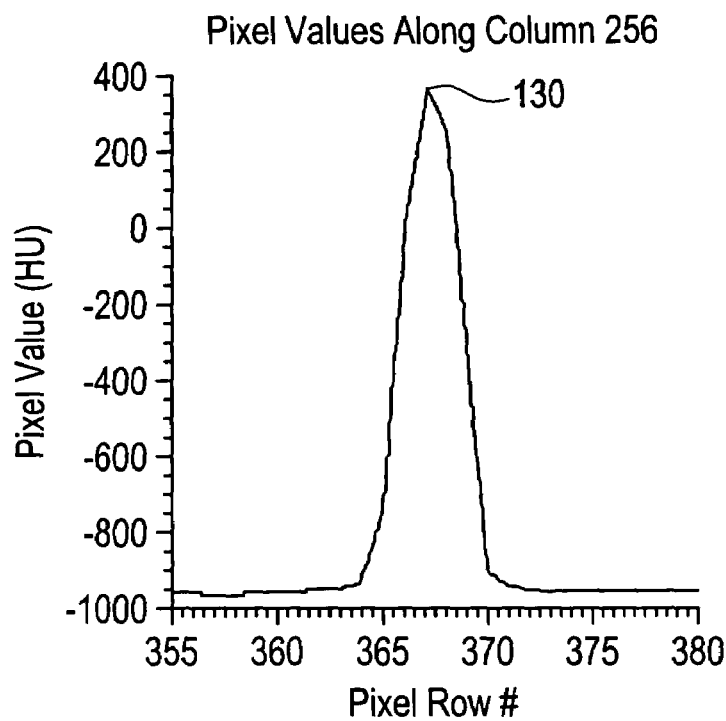
FIG. 7 is a plot of pixel rows versus pixel values in an unloaded table.
Figure 8:
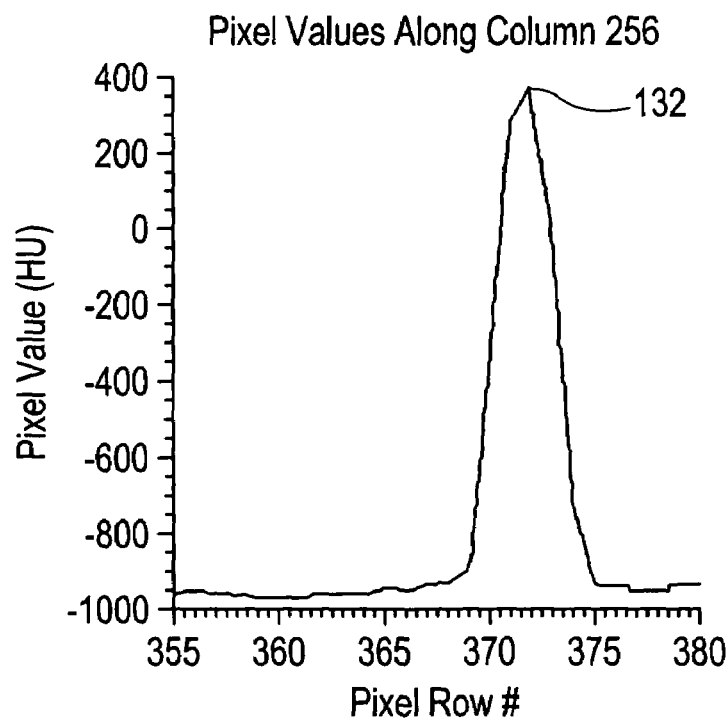
FIG. 8 is a plot of pixel rows versus pixel values in a loaded table.

FIGS. 7 and 8 show plots of the pixel values in Hounsfield Units ("HU") along pixel column 256 for the unloaded and the loaded tables, respectively. Although there are only plots shown along column 256, it should be understood that such plots may be made for a range of pixel columns that intersect the table surfaces, since it is possible that the table may sag at different measurements at different locations. FIG. 7 is with the table unloaded and FIG. 8 is with the anatomical phantom on the table. The first image used to create the plot in FIG. 7 may be considered a "calibration" image. The peak 130 in FIG. 7 is at pixel row 367, that is, the pixel located at row 367, column 256 has the greatest number of Hounsfield units within the column 256 between rows 355 and 380. Pixel row 367 is eight pixel rows away from the predicted location of pixel row 359 calculated above. The difference is likely due to inaccuracies in the initial characterization of the table for an engineering scanner. Nevertheless, the prediction is close enough that only one peak is observed within the plot shown in FIG. 7 (where the plot shows pixel rows 355 to 380) and thus a detection algorithm does not need to sort out other miscellaneous edges that may cause false detections. The peak 132 of the table surface in FIG. 8 is located at pixel row 372, 5 pixels lower in the image than with the unloaded table of FIG. 7 and corresponding to a table sag of 4.9 mm (where 5×0.98=4.9). It should be understood that a higher pixel row number corresponds to a lower vertical position. This agrees well with the graphical measurement of nearly 4 mm made in FIGS. 3 and 4 and is within the error of the graphical measurement, however the pixel row method shown in FIGS. 7–8 is more accurate and more general then the graphical measurement shown in FIGS. 3–4 because it can be implemented to be performed automatically with every image, and does not need to compensate for when the bottom of the image changes locations.

Figure 12:
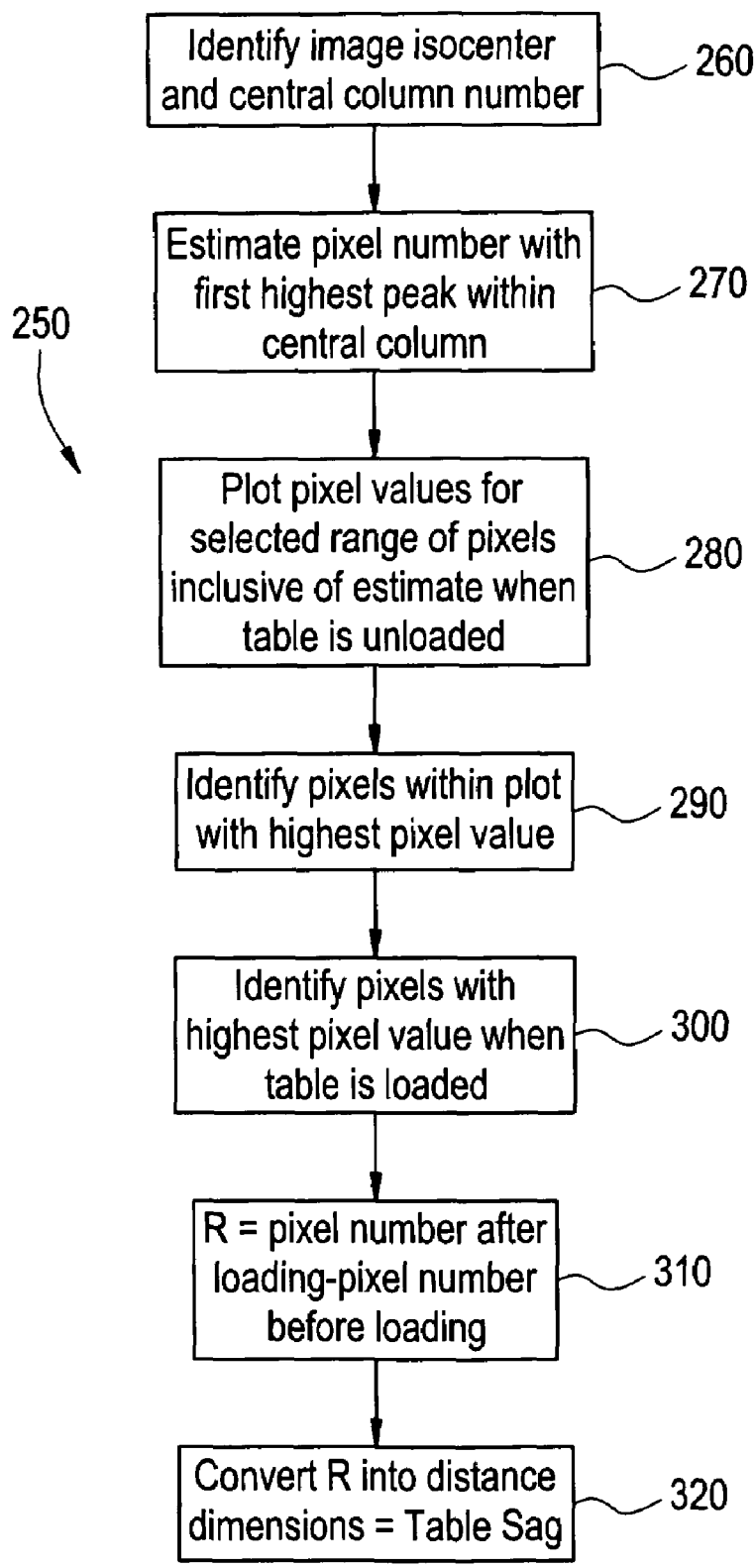
FIG. 12 is a flowchart of another method of measuring table sag.

The feasibility of the algorithm to automatically detect and calculate vertical table sag has thus been demonstrated. The method 250 is shown in FIG. 12 with step 260 being the step of identifying the image isocenter (center pixel), such as 256, 256 may be one of the central pixel numbers, and thus one central column may be column number 256. Another central column may be 257. As described above, the method may be performed on a number of different columns, as the table sag may vary from column to column. The sag from the different columns may be reported as is deemed necessary by the operator. Thus, by "central column", it should be understood that there may be more than one possible column for use in this method. The step 260 may be accomplished by converting the DFOV information into pixels and locating the central area. Step 270 may include estimating the pixel number (corresponding to pixel row number) with the first highest peak within the central column. With the table height information from the DICOM header, the pixel number with the first highest peak within the isocenter column may be estimated by subtracting a pixel conversion of the table height from the isocenter. Step 280 may include plotting pixel values for a range of pixels within the central column, inclusive of the estimate from step 270, when the table is unloaded. Step 290 may include identifying, from the plot of step 280, the pixel number (located within a pixel row within the central pixel column) with the highest pixel value. Step 300 may include identifying the pixel with the highest pixel value when the table is loaded. To accomplish this step, a plot similar to the plot created for step 280 may be made, except with a loaded table. Step 310 may include calculating the difference between the pixel number after loading, from step 300, and the pixel number before loading, from step 290. Step 320 may include calculating the table sag in distance dimensions, such as in mm, by converting the calculation from step 310 into distance dimensions. Although in the particular example, the conversion factor used was 500 mm/512 pixels=0.976 mm/pixel, it should be understood that other systems may rely on different conversion factors.

Thus, the method includes acquiring a first calibration image of the table unloaded, plotting pixel values for a pixel column that intersects the table surfaces, identifying the table surfaces by locating the pixels with the highest pixel value, and computing the vertical location of these pixels. In all subsequent images where the table may be loaded by a patient, the same method is repeated and the pixels corresponding to the table surfaces identified. The vertical location of these pixels is computed and the difference in vertical location compared to the calibration location yields a measurement of the table sag. The calibration scans of an unloaded table may be performed once. After that the table may have varying degrees of sag depending on patient size. Depending on the sag, a different pixel will become the one with the highest pixel value. Identifying this pixel tells us how much the table has sagged. Such identification may occur automatically every time the table is loaded, such as within the computer 34.

Figure 9:
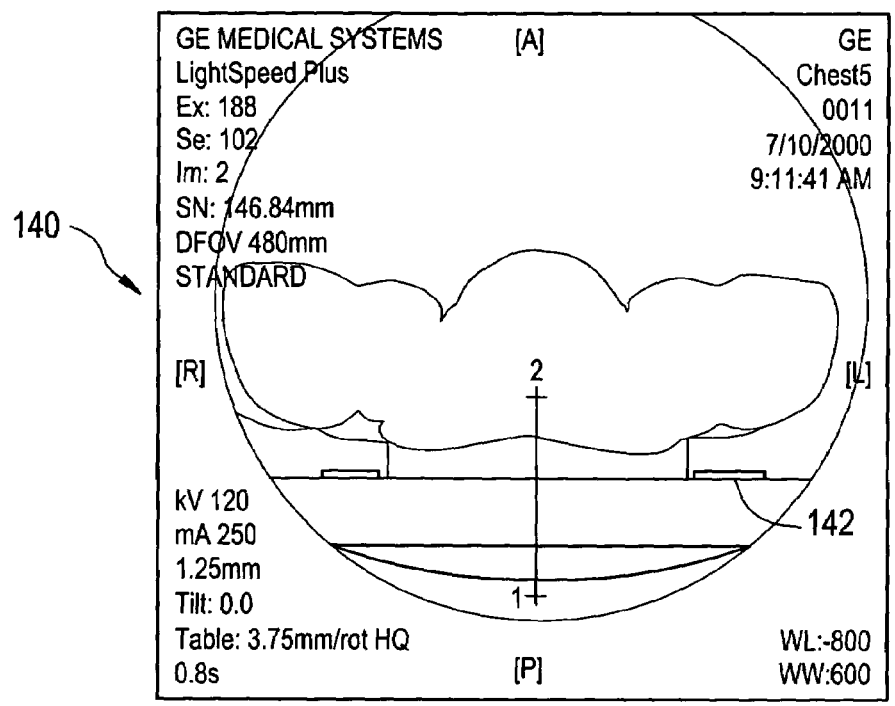
FIG. 9 is an image of a loaded flat table.
Figure 10:
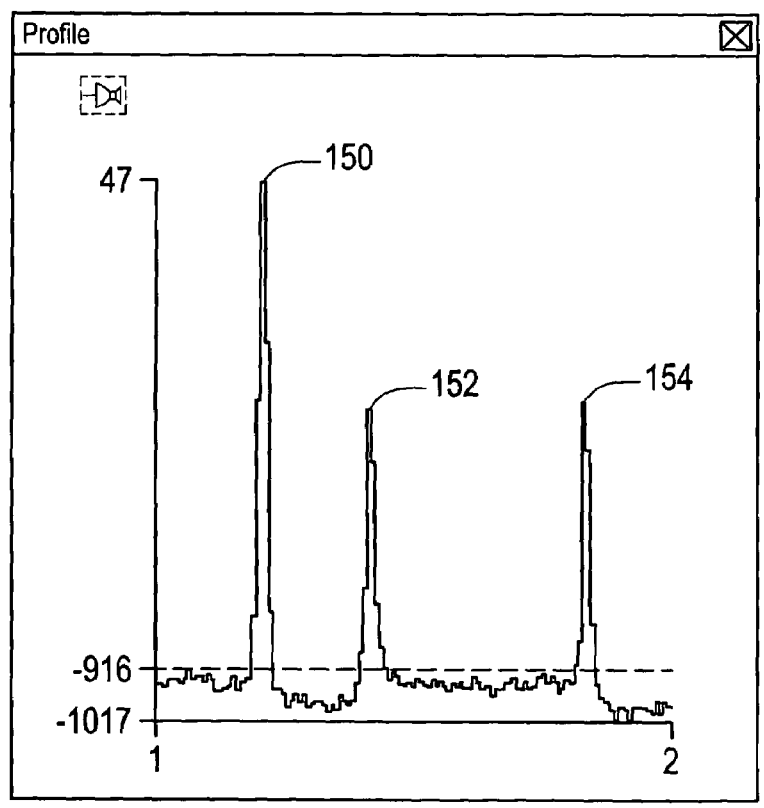
FIG. 10 is a profile of pixel values showing peaks corresponding to table surfaces of the table shown in FIG. 9.

This method may function equally well when a flat top table is installed on top of the curved scanner table. The flat top table is often used in oncology settings. FIGS. 9 and 10 show a flat top table image 140 and a plot of the pixel values through a flat top table 142, respectively. The surfaces in the flat top table 142 are equally straight forward to detect, with the peaks 150, 152, and 154 shown in the plot of FIG. 10 representing the bottom surface, top surface, and padding surface of the table 142 shown in FIG. 9.

At least the top portion of the table, whether straight top or curved top, should be within the display field of view for the algorithm. For a scanner in an oncology setting, such a condition is generally satisfied. The oncology customer generally reconstructs images at the full field of view since all of the anatomical information is needed for radiation therapy planning.

Once the amount of table sag has been calculated, such as 4.9 mm in the described example, there are several corrective actions that may be taken depending on customer preferences. Such actions may range from as little as notifying the user of the situation, to possibly correcting the original image and eliminating the table sag in the images.

This method addresses a concern of customers in oncology settings, as well as other uses, that the patient set-up and resulting images be precise and accurate. In particular, this method allows a measurement of table sag without any additional hardware to be installed in the table.

This method uses a property of existing CT scanner tables, that the surfaces are well-defined edges, to calculate the amount of table sag. Table sag is currently one of the largest sources of patient set-up inaccuracy and this method calculates this error without any additional hardware. A method that does not use the surfaces of the table to calculate the table position would likely require either additional hardware or a special table.

Thus, a system and method has been disclosed that calculates table sag without the necessity of employing additional hardware or specialty tables. The technical effect is a method and system for identifying table sag using image information when the table is loaded. The method may be run using the computer 34 that is present in the CT imaging system 20 and results may be displayed on the monitor 46. Although a specific CT imaging system 20 is disclosed, it is envisioned that this method and system may be employed with alternate imaging systems that utilize a table and may encounter table sag.

The methods and apparatuses of these embodiments may be embodied in the form of computer-implemented processes and apparatuses for practicing those processes. They can also be embodied in the form of computer program code containing instructions embodied in tangible media, such as floppy diskettes, CD-ROMs, hard drives, or any other computer-readable storage medium, wherein, when the computer program code is loaded into and executed by a computer, the computer becomes an apparatus for practicing the invention. The present invention can also be embodied in the form of a computer program code, for example, whether stored in a storage medium, loaded into and/or executed by a computer, or transmitted over some transmission medium, such as over electrical wiring or cabling, through fiber optics, or via electromagnetic radiation or other wireless communication devices, wherein, when the computer program code is loaded into and executed by a computer, the computer becomes an apparatus for practicing the invention. When implemented on a general-purpose microprocessor, the computer program code segments configure the microprocessor to create specific logic circuits.

While embodiments of the invention are described with reference to the exemplary embodiments, it will be understood by those skilled in the art that various changes may be made and equivalence may be substituted for elements thereof without departing from the scope of the invention. In addition, many modifications may be made to the teachings of the invention to adapt to a particular situation without departing from the scope thereof. Therefore, it is intended that the invention not be limited to the embodiment disclosed for carrying out this invention, but that the invention includes all embodiments falling within the scope of the intended claims. Moreover, the use of the terms first, second, etc. does not denote any order of importance, but rather the terms first, second, etc. are used to distinguish one element from another. Furthermore, the use of the terms a, an, etc. do not denote a limitation of quantity, but rather denote the presence of at least one of the referenced items.

What is claimed is:

1. A method for measuring table sag of a table, the method comprising:
   identifying pixel values of pixels from a column in a loaded table image and in an unloaded table image; and,
   calculating a difference between pixel row numbers having highest pixel values in the loaded table image and unloaded table image for determining how many pixel rows the table has sagged from the unloaded image to the loaded image.

2. The method of claim 1 further comprising:
   acquiring a first image of the table unloaded;
   plotting pixel values for a range of pixels in the column from the first image in a first plot;
   identifying a first pixel within the first plot that has a highest pixel value, the first pixel identified by a row number and column number;
   acquiring a second image of the table loaded;
   plotting pixel values for a range of pixels in the column from the second image in a second plot;
   identifying a second pixel within the second plot that has a highest pixel value, the second pixel identified by a row number and a column number;
   calculating a difference between the row number of the second pixel and the row number of the first pixel; and,
   converting the difference into a measurement of table sag.

3. The method of claim 2 wherein the column is a central column of the first and second images, and further comprising, prior to plotting pixel values for a range of pixels in a first plot, estimating a pixel row number within the first image having a highest peak pixel value within the central column of the first image, wherein the range of pixels in the first plot includes the pixel estimated to have the highest peak pixel value.

4. The method of claim 3 further comprising, prior to estimating a pixel row number within the first image having a highest peak pixel value within the central column, identifying an isocenter of the first image.

5. The method of claim 3 further comprising, prior to estimating a pixel row number within the first image having a highest peak pixel value within the central column, using table height information from a header within the first image to estimate the pixel row within the first image having a highest peak pixel value within the central column.

6. The method of claim 5 further comprising converting the table height information into pixels and calculating a difference between the table height information converted into pixels and an isocenter pixel number of the image.

7. The method of claim 1 wherein table sag is automatically calculated when the table is loaded.

8. The method of claim 1 performed by a computer within a CT imaging system.

9. The method of claim 8 wherein the measurement of table sag is displayed on a monitor within the CT imaging system.

10. The method of claim 1 further comprising converting the difference into a first measurement of table sag, and further comprising:
calculating a distance A from a point x in the unloaded table image to a surface of the table in the unloaded table image;
calculating a distance B from a point x in the loaded table image to a surface of the table in the loaded table image;
calculating the difference between distance A and distance B to represent a second measurement of table sag and comparing the first measurement to the second measurement.

11. The method of claim 10 wherein the point x is selected within a central column within the images.

12. The method of claim 11 wherein the distance A and the distance B are located within the central column.

13. A storage medium encoded with machine-readable computer program code for measuring table sag of a table, the storage medium including instructions for causing a computer to implement a method comprising:
identifying pixel values of pixels from a column in a loaded table image and in an unloaded table image; and,
calculating a difference between pixel row numbers having highest pixel values in the loaded table image and unloaded table image for determining how many pixel rows the table has sagged from the unloaded image to the loaded image.

14. The storage medium of claim 13 further comprising instructions for causing a computer to implement:
acquiring a first image of the table unloaded;
plotting pixel values for a range of pixels in the column from the first image in a first plot;
identifying a first pixel within the first plot that has a highest pixel value, the first pixel identified by a row number and column number;
acquiring a second image of the table loaded;
plotting pixel values for a range of pixels in the column from the second image in a second plot;
identifying a second pixel within the second plot that has a highest pixel value, the second pixel identified by a row number and a column number;
calculating a difference between the row number of the second pixel and the row number of the first pixel;
converting the difference into a measurement of table sag.

15. The storage medium of claim 14 further comprising instructions for causing a computer to implement, prior to plotting pixel values for a range of pixels in a first plot, estimating a pixel row number within the first image having a highest peak pixel value within a central column of the first image, wherein the range of pixels in the first plot includes the pixel estimated to have the highest peak pixel value.

16. The storage medium of claim 15 further comprising instructions for causing a computer to implement, prior to estimating a pixel row number within the first image having a highest peak pixel value within the central column, identifying an isocenter of the first image.

17. The storage medium of claim 15 further comprising instructions for causing a computer to implement, prior to estimating a pixel row number within the first image having a highest peak pixel value within the central column, using table height information from a header within the first image to estimate the pixel row within the first image having a highest peak pixel value within the central column.

18. The storage medium of claim 17 further comprising instructions for causing a computer to implement converting the table height information into pixels and calculating a difference between the table height information converted into pixels and an isocenter pixel number of the image.

19. The storage medium of claim 13 further comprising instructions for causing a computer to implement automatic table sag calculation when the table is loaded.

20. A computer for use in an imaging system, the computer comprising a computer readable medium having computer readable program code means embodied in the medium, the computer readable program code means for:
receiving digital images from an image reconstructor in the imaging system; and
calculating, using information provided from the digital images received by the computer, table sag of a support table used within the imaging system;
wherein the calculated table sag is usable for correcting an original image of the digital images and eliminating the table sag in the images.

21. The computer of claim 20 wherein the digital images received by the computer include a first image of the table unloaded and a second image of the table loaded, wherein the computer provides a first plot plotting pixel values for a range of pixels within a selected column in the first image and a second plot plotting pixel values for a range of pixels within the selected column in the second image, wherein the table sag is measured by calculating a difference between a first pixel row number in the first plot and a second pixel row number in the second plot having highest pixel values in each plot and converting the difference into a measurement of table sag.

22. An imaging system comprising:
an x-ray source;
an x-ray detector array for receiving an x-ray beam from the x-ray source;
a data acquisition system for receiving signals from the x-ray detector array;
an image reconstructor for receiving signals from the data acquisition system and for generating digital images;
a table for supporting a person or object adjacent the x-ray source; and,
a computer for receiving the digital images from the image reconstructor, wherein table sag is calculated only within the computer using information provided from the digital images.

23. The imaging system of claim 22 wherein the digital images include a first image of the table unloaded and a second image of the table loaded, wherein the computer provides a first plot plotting pixel values for a range of pixels within a selected column in the first image and a second plot plotting pixel values for a range of pixels within the selected column in the second image, wherein the table sag is measured by calculating a difference between a first pixel row number in the first plot and a second pixel row number in the second plot having highest pixel values in each plot and converting the difference into a measurement of table sag.

* * * * *